United States Patent [19]
Collins et al.

[11] Patent Number: 4,652,529
[45] Date of Patent: Mar. 24, 1987

[54] SERUM PRETREATMENT FOR TRICYCLIC ANTIDEPRESSANT DRUG ASSAYS

[75] Inventors: Christine G. Collins, San Jose; Susan Pankey; Anna Jaklitsch, both of Palo Alto, all of Calif.

[73] Assignee: Syntex (U.S.A.) Inc., Palo Alto, Calif.

[21] Appl. No.: 657,319

[22] Filed: Oct. 2, 1984

[51] Int. Cl.⁴ .................. G01N 30/02; G01N 33/50
[52] U.S. Cl. .................................... 436/92; 210/656; 210/96.1; 210/161; 210/178
[58] Field of Search ................ 436/92, 96, 161, 174, 436/178; 210/656

[56] References Cited

U.S. PATENT DOCUMENTS 4,223,013 9/1980 Hu et al. .
4,275,160 6/1981 Singh et al. .
4,307,245 12/1981 Hu et al. .
4,551,275 11/1985 Piro et al. .

OTHER PUBLICATIONS

Narasimhachari, Journal of Chromatography, 225 (1981) 189-195.
Thoma et al, Therapeutic Drug Monitoring, 1:335-358, 1979.
Kabra et al, "Clinical Liquid Chromatography—vol. 1, Analysis of Exogenous Compounds"; CRC Press, Inc; Boca Raton, Fla.; 1984, pp. 197-208.
Norman et al., J. Chromatography, 340 (1985) 173-197.
Narasimhachari, Chemical Abstracts, vol. 95; No. 161629P; 1981.
Gifford et al., J. of Chrom., 105, 107-113 (1975).
Gupta et al., Clin Biochem, 9, 247-51 (1956).
Nyberg & Martenson, J. Chrom 143, 491 (1977).
Watson & Stewart, J. Chrom, 132, 134, 155-159, 182 (1977).
Aherne, et al., Br. J. Clin. Pharmac., 3, 561 (1976).
Turner, Lancet, 180, 1316 (1977).
Aherne et al., Lancet, 180, 1214 (1977).
Hubbard et al., J. Pharm. Sc., 67, 1571-1578 (1978).
Hubbard et al., Canadian J. of Pharm. Sc., 15, 89-93 (1980).

Primary Examiner—Arnold Turk
Attorney, Agent, or Firm—Theodore J. Leitereg; Carole F. Barrett

[57] ABSTRACT

Serum is passed through a column containing alkylated silica gel. The column is then washed with a mixture comprising from about 50 to 85 volume percent of an aqueous buffered medium of pH from about 3.5 to 5.0 and from about 15 to 50 volume percent of an organic solvent containing from 1 to 6 carbon atoms and from 1 to 5 heteroatoms selected from the group consisting of oxygen, nitrogen, and sulfur. The tricyclic antidepressant drug is removed from the column with an eluent mixture comprising from about 0 to 75 volume percent of an aqueous buffered medium of pH of about from 6 to 8 and from about 25 to 100 volume percent of one or more organic solvents containing from 1 to 6 carbon atoms and from 1 to 5 heteroatoms selected from the group consisting of oxygen, nitrogen, and sulfur. In this way, a tricyclic antidepressant drug sample, free from interfering metabolites, for use in assay determinations is obtained.

19 Claims, No Drawings

SERUM PRETREATMENT FOR TRICYCLIC ANTIDEPRESSANT DRUG ASSAYS

BACKGROUND OF THE INVENTION

1. Field of the Invention

A number of tricyclic compounds find use in the treatment of depression. These tricyclic antidepressants include imipramine, desmethylimipramine (desipramine), amitriptyline, nortriptyline, protriptyline, doxepin and desmethyldoxepin (nordoxepin). In administering a tricyclic antidepressant, it is frequently necessary to ensure that the blood level of the antidepressant remains within a certain narrow concentration range in order to ensure effective dosage, while avoiding levels which may be toxic or produce undesirable effects. Furthermore, it is often necessary to detect potentially toxic levels of tricyclic antidepressants and their metabolites.

It is therefore desirable to provide a simple and rapid procedure for determining or detecting the levels of tricylic antidepressants in serum or other physiological fluids. The procedure should provide reproducible values and be specific for the tricyclic compounds which are measured. Thus, the procedure must be capable of distinguishing the tricyclic antidepressants from other drugs and from metabolites of the tricyclic antidepressant drug, which would otherwise give an erroneous result in any assay for the detection of tricyclic antidepressants.

Since the therapeutic range of the tricylic antidepressant drugs is from about 50 to 300 ng/ml, it is necessary not only to measure extremely small amounts of the tricyclic antidepressant drug in serum, but also to be able to distinguish between small differences in concentrations. Naturally occurring materials or metabolites of the tricyclic antidepressant drug in the serum sample may modify the observed signal so as to give falsely high results. It would therefore be desirable to provide for a simple means for pretreatment of a serum sample for a tricyclic antidepressant drug assay. The pretreatment method should be rapid and efficient and provide an assay sample containing the drug substantially free of interfering substances.

2. Brief Description of the Prior Art

The tricyclic antidepressants are closely related chemically to one another. Techniques reported for the determination of amitriptyline in biological fluids include the use of thin layer chromatography, gas-liquid chromatography and GLC-mass spectrometry. Gifford, et al., *J. of Chrom.*, 105, 107–113 (1975); Gupta et al., *Clin. Biochem.*, 9, 247–51 (1976); Nyberg and Martensson, *J. Chromatography*, 143, 491 (1977); Watson and Stewart, *J. Chrom.*, 134, 182 (1977); ibid. 132 155–159 (1977). Radioimmunnoassay has been reported for amitriptyline by Aherne, et al., *Br. J. Clin. Pharmac.*, 3, 561 (1976), Turner, *Lancet*, 180, 1316 (1977); and Aherne, et al., Lancet 1214 (1977). In Aherne, et al., ibid., a synthesis for an antigen for use as an immunogen for antibody formation is described, where nortriptyline is substituted with aminobutylene followed by conjugation to bovine serum albumin employing carbodiimide. In another antigen conjugate synthesis by Kaul, et al., *J. Anal. Tox.*, 1, 236 (1977), nortriptyline was conjugated to bovine serum albumin through a succinyl group. The resulting antibodies were found to have significant cross-reactivity with a number of other tricyclic drugs.

U.S. Pat. No. 4,275,160 describes imipramine derivatives and poly(amino acid) conjugates. U.S. Pat. Nos. 4,223,013 and 4,307,245 disclose amitriptyline conjugates to antigenic proteins and enzymes.

N-(2-carboxyethyl) derivatives of nortriptyline and desipramine are disclosed by Hubbard et al., *J. Pharm. Sc.*, 67, pp. 1571–1578 (1978) and by Hubbard et al., *Canadian Journal of Pharmaceutical Sciences*, 15, pp. 89–93 (1980).

Tricyclic antidepressant conjugates to antigens and enzymes are disclosed in U.S. patent application Ser. No. 522,887, filed Aug. 12, 1983.

SUMMARY OF THE INVENTION

Serum samples for tricyclic antidepressant drug assays are pretreated by passing the serum sample through a column containing silica gel that is alkylated. After application of the serum sample, the column is washed with a wash mixture comprising from about 15 to 50 volume percent of an organic solvent containing from 1 to 6 carbon atoms and from 1 to 5 heteroatoms selected from the group consisting of oxygen, nitrogen, and sulfur and from about 50 to 85 volume percent of an aqueous buffered solution having a pH of from about 3.5 to 5.0. The drug is eluted from the column with an eluent comprising from about 25 to 100 volume percent of an organic solvent of from 1 to 6 carbon atoms and from 1 to 5 heteroatoms selected from the group consisting of oxygen, nitrogen, and sulfur and from about 0 to 75 volume percent of an aqueous buffered solution having a pH of about from 6 to 8. The eluted material contains the tricyclic antidepressant drug substantially free of interfering substances. The pretreatment method finds particular application in conjunction with assays employing enzyme or fluorescent labels.

DESCRIPTION OF THE SPECIFIC EMBODIMENTS

Blood serum or plasma samples for tricyclic antidepressants drug assays are pretreated to provide a sample substantially free from metabolites present in the serum sample and in a form useful for a tricyclic antidepressant drug assay determination. By the term "substantially free" is meant that the tricyclic antidepressant drug sample contains less than about from 20%, preferably less than about from 10%, of metabolites of such drug.

The method normally employs liquid chromatography using a column containing silica gel alkylated with alkyl groups of from 1 to 12 carbon atoms, preferably 1 to 6 carbon atoms. The silica gel particles have a size in the range of about 30–50 $\mu$m, preferably about 40 $\mu$m. The particles are silanized with methyl or ethyl silyl groups to provide the alkylated silica gel particles.

The amount of the column packing, i.e., alkylated silica gel, employed and the dimensions of the column are dependent on the size of the serum sample to be treated. Generally, for a serum sample of 0.5 ml, about 80 to 120 mg, preferably 90 to 110 mg, of packing is used. For 100 mg of silica gel, depending upon the manner of packing, as well as the diameter of the column, the height of the column can vary from about 6 to 10 mm.

The column is packed by introducing the silica gel powder into an appropriate column. The column is then conditioned, by adding an alcohol, such as methanol, and removing the alcohol by any convenient means, e.g., vacuum, positive pressure, centrifugation, or the like. After the alcohol has been removed, the column is then washed with water, preferably deionized water. The water is then removed as described above, and the column is now ready for the sample.

Prior to applying the sample to the column, the serum sample may be subjected to other pretreatments. Depending upon the nature of the sample, the sample may be centrifuged, or the like.

The sample is then added to the column after all the excess methanol and water employed in the pretreatment and washing of the column have been removed. The sample may then be drawn into the column by vacuum or centrifugation, or it may be pushed into the column by positive pressure. The conditions for applying the sample to the column will be generally mild, for example, a vacuum in the range of about 10–20 inches Hg may be used. Various conventional devices can be used, for example, the Vac-Elut® vacuum box (Analytichem International).

After the sample has been applied to the column, the column is washed with a mixture comprising a water soluble organic solvent and an aqueous buffered medium. The organic solvent generally has from 1 to 6, preferably 1 to 3, carbon atoms and from 1 to 5, preferably 1 to 2, heteroatoms selected from the group consisting of oxygen, nitrogen and sulfur. The organic solvent may be an alkylnitrile such as acetonitrile, propionitrile, an alcohol such as methanol, ethanol, propanol, a ketone such as acetone, and the like. The wash mixture generally contains from about 15 to 50, preferably 25 to 35, volume percent of the organic solvent.

The wash mixture also contains from about 50 to 85, preferably 65 to 75, volume percent of an aqueous buffered medium having a pH of from about 3.5 to 5.0, preferably from about 4.0 to 4.4. The buffered medium may be about 0.1 to 1M, preferably 0.2 to 0.4M, in a metal salt of a carboxylic acid having from 2 to 4 carbon atoms. Exemplary of such metals are alkali metals such as sodium, potassium, and the like and exemplary of carboxylic acids are acetic acid, propionic acid, and the like.

The aqueous buffered medium portion of the column wash mixture may also contain an alkyl sulfonate wherein the alkyl group has from 5 to 7 carbon atoms such as, for example, pentane sulfonate, hexane sulfonate, heptane sulfonate, and the like. Conveniently, the alkyl sulfonate is incorporated into the mixture as part of the aqueous buffered medium. In this mode, the aqueous buffered medium would be from about 0 to 0.010M in alkyl sulfonate.

The volume of the wash mixture should be sufficient to remove substantially all of the metabolites of the tricyclic antidepressant drug from the column. However, the wash mixture should remove substantially none of the drug itself. The volume of the wash solution is based primarily on the number of theroetical plates of the column packing. As an example, the volume of wash mixture can be from about 0.8 to 1.0 ml for about 100 mg of column packing. After addition of the wash solution, the wash solution may be drawn through the column as described above for the sample. Usually this will involve, for an initial volume of 1 ml sample, at least about 15 seconds and not more than about two minutes, generally from about 20 seconds to 45 seconds. Any water remaining at the tip of the column may be removed by blotting or other convenient means.

The tricyclic antidepressant drug is then eluted to provide for a tricyclic antidepressant drug sample substantially free from metabolites to be used in an assay. To this end an elution mixture is employed comprising one or more water soluble organic solvents and an aqueous buffered medium having a pH of from about 6 to 8, preferably, 6.5 to 7.5, more preferably neutral pH. The organic solvent usually comprises from about 25 to 100, preferably 70 to 80, volume percent of the elution mixture and the aqueous buffered medium usually comprises from about 0 to 75, preferably 20 to 30, volume percent of the elution mixture. Generally, the organic solvent has the same characteristics as those described above for the wash mixture and, conveniently, may be the same organic solvent as that employed in the wash mixture. Preferably, the elution mixture comprises at least two organic solvents as defined above in a ratio of about from 1:1 to 1:2. A preferred elution mixture may contain from about 45 to 55 volume percent of an alkylnitrile as defined above and from about 25 to 35 volume percent of an alcohol as defined above for the organic solvent.

The aqueous buffered medium may comprise a phosphate buffer such as potassium hydrogen phosphate. The phosphate may conveniently be combined with the water prior to combination with the other eluent components. In this embodiment, the aqueous medium is usually about from 0 to 0.01M in phosphate buffer.

Elution is accomplished by adding from about 0.5 to 1.0 ml of the eluent mixture for an initial volume of 1 ml of serum sample. Generally, the volume of eluent mixture should be sufficient to remove substantially all of the drug from the column; usually the volume corresponds to the initial volume of the serum sample. The eluent is drawn through the column in the same manner described above for the wash mixture. The eluate is then collected and is ready to be used in an assay since it contains the tricyclic antidepressant drug substantially free of interfering substances, i.e., those substances which, by their presence in the sample, would affect the accuracy of the assay.

It is also within the scope of the present invention to dilute the eluate prior to conducting an assay. Generally, about 0.5 to 1 ml of an aqueous buffer of pH 5 to 8, such as Tris HCl buffer is passed through the column from which the sample was eluted. The buffer is then combined with the eluted sample.

In assays involving labels, e.g., enzyme labels, the components of the wash mixture and of the eluant should have little or no detrimental effect on the label activity.

Tricyclic antidepressant drugs, for which samples treatable by the method of the present invention are assayed, are derivatives of dibenzazepine, dibenzocycloheptadiene, and dibenzoxepin and generally have the following formula:

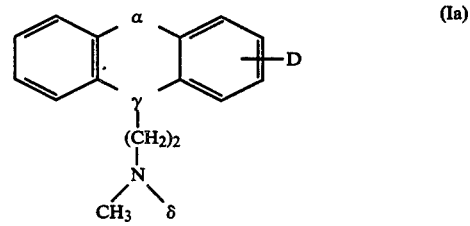

(Ia)

wherein:

α is $CH_2-CH_2$, $CH_2-CH(OH)$, $CH=CH$, or $CH_2-O$;

γ is N—CH$_2$, C=CH, or N—CH(R) wherein R is alkyl of 1 to 3 carbon atoms, particularly CH$_3$;

δ is H or CH$_3$; and

D is hydrogen, hydroxy, or a halogen atom of atomic number 9 to 53, preferably 7 to 35, more preferably a chlorine atom.

Exemplary of such tricyclic antidepressant compounds are imipramine, desmethylimipramine, amitriptyline, nortriptyline, protriptyline, trimipramine, chlomipramine, doxepin and desmethyldoxepin.

Serum samples treated to give tricyclic antidepressant drug extracts in accordance with the present invention may be assayed for the presence of the drug by a number of assay methodologies. The assays may be heterogeneous or homogeneous involving labels such as enzymes, radioisotopes, fluorescers, and the like.

The invention also includes a kit comprising, in a packaged combination, (1) a prepacked column having dimensions as described above and containing silica gel, alkylated with alkyl groups containing from 1 to 12 carbon atoms, in amounts as described above, to which column the serum sample is to be applied, (2) from 100 to 200 ml of a wash mixture as described above, and (3) from 100 to 200 ml of an eluent as described above. The wash mixture and the eluent may be in suitable containers such as vials made of a suitable material such as glass or plastic. The kit may also include ancillary items such as a device for securing the serum sample or applying the serum sample to the column, column conditioning solutions as described above, wash solutions such as an alcohol, deionized water, 100 to 200 ml of a post elution aqueous buffer as described above, etc., in separate containers and so forth. The above kit may be combined with an assay kit for performing a tricyclic antidepressant drug assay or it may be separate therefrom.

EXAMPLE

The invention is further demonstrated by the following illustrative example, which is provided by way of illustration and not limitation.

EXAMPLE 1

Assay for Nortriptyline

A 100 mg C-2 column from Analytichem International are washed with approximately one ml of methanol followed by approximately one ml of water. The sample (500 μl) was placed on the top of the column. A vacuum apparatus was attached to the bottom and a vacuum was drawn on the column. The eluate obtained was discarded and the column was washed with 900 μl of a solution which was 70% 0.4M sodium acetate, 5 mM heptane sulfonate, pH 4.2, and 30% acetonitrile. A vacuum was again drawn on the column and the eluate was discarded. Next, the column was contacted with 500 μl of a solution which was 50% acetonitrile, 25% methanol, and 25% 5 mM K$_2$HPO$_4$, pH 7. The eluant was collected and used in the assay procedure.

An enzyme conjugate and an antibody reagent were prepared in accordance with the teaching of U.S. patent application Ser. No. 613,709, filed May 23, 1984, the disclosure of which is incorporated herein in its entirety by reference thereto. In carrying out the assay, a Gilford Stasar III microsample spectrophotometer was employed with a Thermocuvette with a flow cell. All readings were made at 340 mn. The following solutions were prepared as reagents for use in the assay.

Buffer:
0.055M tris-HCl pH 8.1 (RT)

Enzyme Conjugate Reagent:
Buffer
0.9% NaCl
1.0% β-lactoglobulin (BLG), pH 8.0 (RT)
Sufficient enzyme conjugate to give a maximum rate of ΔOD equal to 700–1200 in the assay medium Assay buffer:
Buffer
0.5% NaCl
0.01% (v/v) Triton X-100, pH 8.0 (RT)

Antibody Reagent:
Buffer
0.1% BLG,
G-6-P(Na) 0.198M,
Nicotine adenine dinucleotide (NAD) 0.12M, pH 5.2 (RT)
Antinortriptyline optimized for assay (antibodies prepared in sheep). All % indicated are w/v, g/100 ml.

The protocol employed for carrying out an assay was as follows:

Into a diluter was drawn 15 microliters (μl) of the above sample. The sample was dispensed with 250 microliters of the assay buffer into a one milliliter Croan cup followed by 15 μl of the antibody reagent with 250 μl of the assay buffer. After 50 sec. incubation 15 μl of the enzyme reagent and 250 μl of the assay buffer were added. Immediately after the enzyme addition, the entire sample was aspirated into the flow cell. After 10 seconds, a first reading was taken, followed by a second reading after a 50 second interval. The results are reported as the difference in absorbance X 2.667.

| Sample Concentration of Nortriptyline (ng/ml) | ΔOD |
|---|---|
| 0 | 695* |
| 25 | 723 |
| 50 | 761 |
| 100 | 807 |
| 175 | 850 |
| 250 | 870 |

*Lowest rate in assay with predetermined amount of antibody.

EXAMPLE 2

Assay for Desmethylimipramine

A 100 mg column (C-2 from Analytichem, Harbor City, Calif.) was washed with approximately one ml of methanol followed by approximately one ml of water. The sample (500 μl) was placed on the top of the column. A vacuum apparatus was attached to the bottom and a vacuum was drawn on the column. The eluate obtained was discarded and the column was washed with 900 μl of a solution which was 70% 0.4M sodium acetate and 5 mM heptane sulfonate, pH 4.2, 30% acetonitrile. A vacuum was again drawn on the column and the eluate was discarded. Next, the column was contacted with 500 μl of a solution which was 50% acetonitrile, 25% methanol, and 25% 5 mM K$_2$HPO$_4$, pH 7. The eluant was collected and used in the assay procedure.

The antibodies and the enzyme conjugate employed in this assay for desmethylimipramine were prepared in accordance with the teaching of U.S. patent application Ser. No. 592,492, filed Mar. 23, 1984, the disclosure of which is incorporated herein in its entirety by reference thereto. In carrying out the assay, a Gilford Stasar III ® microsample spectrophotometer was employed with a Thermocuvette (3017T) with a flow cell. All readings were made at 340 nm. The following solutions were prepared as reagents for use in the assay.

Buffer:
0.055M tris-HCl pH 8.0 (RT)
Enzyme Conjugate Reagent:
Buffer
0.9% NaCl
1.0% BLG, pH 8.0 (RT)
Sufficient enzyme conjugate to give a maximum rate of ΔOD equal to 800-1200 in the assay medium
Assay buffer:
Buffer
0.5% NaCl
0.01% (v/v) Triton X-100, pH 8.0 (RT)
Antibody Reagent:
Buffer
0.1% BLG,
G-6-P(Na) 0.22M,
NAD 0.13M, pH 5.2 (RT).
Antidesmethylimipramine optimized for assay (antibodies were prepared in sheep)
(All % indicated are w/v, g/100 ml.)

The protocol employed for carrying out an assay was as follows:

Into a diluter was drawn 15 microliters (μl) of the above eluant. This sample was dispensed with 250 microliters of the assay buffer into a one milliliter Croan cup followed by 15 μl of the antibody reagent with 250 μl of the assay buffer. After 50 sec. incubation 15 μl of the enzyme reagent and 250 μl of the assay buffer were added. Immediately after the enzyme addition, the entire sample was aspirated into the flow cell. After 10 seconds, a first reading is taken, followed by a second reading, after a 50 second interval. The results are reported as the difference in absorbance×2.667.

| Sample Concentration of Desmethylimipramine (ng/ml) | ΔOD |
|---|---|
| 0 | 702* |
| 50 | 737 |
| 100 | 765 |
| 200 | 800 |
| 350 | 834 |
| 500 | 854 |

*lowest rate in assay with predetermined amount of antibody.

The assay of Example 1 was repeated except that the serum sample was not pretreated in accordance with the present invention. The following represents a statistical summary of the results where the y-axis represents the enzyme-label assay result and the x-axis represents a reference method conducted using high pressure liquid chromatography (HPLC).

| | Nortriptyline | |
|---|---|---|
| | Pretreated Sample | Non-pretreated Sample |
| n | 14 | 12* |
| slope | 1.11 | 2.36 |
| intercept | 10.39 | 87.46 |
| correlation | .98 | .83 |
| SEE | 9.2 | 26.7 |

*Two samples had rates higher than the highest calibrator and therefore could not be accurately quantitated.

It is evident from the above results that the subject method provides a sample allowing for an accurate assay for tricyclic antidepressant drugs, particularly involving enzyme labels. Thus, a sensitive and efficient method is provided for treating samples for tricyclic antidepressant drug assays which results in accurate determinations of the drug.

Although the foregoing invention has been described in some detail by way of illustration and example for purposes of clarity of understanding, it will be obvious that certain changes and modifications may be practiced within the scope of the appended claims.

What is claimed is:

1. A method for preparing a serum sample for determination of a tricyclic antidepressant drug in an assay, which method comprises:
   (a) adding said serum sample to a chromatographic column containing silica gel alkylated with alkyl groups of from 1 to 12 carbon atoms;
   (b) washing the column with a wash solution comprising from about 15 to 50 volume percent of a first organic solvent of from 1 to 6 carbon atoms and from 1 to 5 heteroatoms selected from the group consisting of oxygen, nitrogen, and sulfur and from about 50 to 85 volume percent of an aqueous buffered medium having a pH of about from 3.5 to 5.0, in an amount sufficient to substantially remove metabolites of the tricyclic antidepressant drug from said column but insufficient to remove the tricyclic antidepressant drug from the column; and
   (c) eluting the tricyclic antidepressant drug with an elution solution comprising from about 25 to 100 volume percent of a second organic solvent of from 1 to 6 carbon atoms and 1 to 5 heteroatoms selected from the group consisting of oxygen, nitrogen, and sulfur, wherein said second organic solvent may be the same or different than said first organic solvent, and from about 0 to 75 volume percent of an aqueous buffered medium having a pH of from about 6 to 8 in an amount sufficient to elute a substantial portion of the tricyclic antidepressant drug from the column.

2. The method of claim 1 wherein the silica gel is alkylated with alkyl groups of from 1 to 6 carbon atoms.

3. The method of claim 2 wherein said alkyl group is ethyl.

4. The method of claim 1 wherein at least one of said first and said second organic solvents is an alkylnitrile.

5. The method of claim 1 wherein at least one of said first and second organic solvents is acetonitrile.

6. The method of claim 1 wherein said aqueous buffered medium in Step b contains a metal salt of a carboxylic acid.

7. The method of claim 6 wherein said metal salt is sodium acetate.

8. The method of claim 1 wherein said aqueous buffered medium in Step b additionally contains an alkyl sulfonate of from 5 to 7 carbon atoms.

9. The method of claim 8 wherein said alkyl sulfonate is heptane sulfonate.

10. The method of claim 1 wherein said aqueous buffered medium in Step b has a pH of about 4.0 to 4.5.

11. The method of claim 1 wherein the amount of wash solution is about 0.8 to 1.0 ml.

12. The method of claim 1 wherein the amount of elution solution is about 0.5 to 1.0 ml.

13. The method of claim 1 wherein the elution solution in Step c comprises two different organic solvents in the ratio of about 1:1 by volume to 1:2 by volume.

14. The method of claim 13 wherein the organic solvents are an alkylnitrile and an alcohol.

15. The method of claim 13 wherein the organic solvents are acetonitrile and methanol.

16. The method of claim 1 wherein the aqueous buffered medium in Step c is an aqueous phosphate buffer.

17. The method of claim 1 wherein said tricyclic antidepressant drug is selected from the group consisting of amitriptyline, nortriptyline, impramine, desmethylimipramine, doxepin and desmethyldoxepin.

18. The method of claim 1 wherein in Step b the wash solution comprises from about 25 to 35 volume percent of the organic solvent and from about 65 to 75 volume percent of the aqueous buffered medium.

19. The method of claim 1 wherein in Step c the elution solution comprises from about 65 to 75 volume percent of the organic solvent and from about 25 to 35 volume percent of the aqueous buffered medium.

* * * * *